United States Patent
Ge et al.

(10) Patent No.: US 8,518,429 B2
(45) Date of Patent: Aug. 27, 2013

(54) ARSENIC TRIOXIDE MEDICAL ELUTION SCAFFOLD

(75) Inventors: Junbo Ge, Shanghai (CN); Xiaoyi Ma, Beijing (CN)

(73) Assignee: Beijing Amsino Medical Co., Ltd., Beijing (CN)

( * ) Notice: Subject to any disclaimer, the term of this patent is extended or adjusted under 35 U.S.C. 154(b) by 377 days.

(21) Appl. No.: 12/681,097

(22) PCT Filed: Apr. 21, 2008

(86) PCT No.: PCT/CN2008/070760
§ 371 (c)(1),
(2), (4) Date: Mar. 31, 2010

(87) PCT Pub. No.: WO2009/067862
PCT Pub. Date: Jun. 4, 2009

(65) Prior Publication Data
US 2010/0247603 A1    Sep. 30, 2010

(30) Foreign Application Priority Data

Nov. 27, 2007  (CN) .......................... 2007 1 0171085

(51) Int. Cl.
*A61F 2/00* (2006.01)
(52) U.S. Cl.
USPC .......................................... 424/423; 424/426
(58) Field of Classification Search
None
See application file for complete search history.

(56) References Cited

U.S. PATENT DOCUMENTS

2004/0249450 A1  12/2004 Ishii
2007/0207186 A1*  9/2007 Scanlon et al. ............... 424/424

FOREIGN PATENT DOCUMENTS

| CN | 1398585 A | | 2/2003 |
| CN | 1657023 A | * | 8/2005 |
| CN | 1669597 A | | 9/2005 |
| CN | 1223385 C | | 10/2005 |
| WO | WO 2007/065016 A2 | | 6/2007 |

OTHER PUBLICATIONS

Office Action, mailed Apr. 3, 2012, for JP Application No. 2010-528264.
Extended European Search Report, mailed Feb. 24, 2011, for EP 08734118.6-1219.
Office Action, mailed Dec. 27, 2011, for EP 08734118.6-1219.
Database WPI, Week 200604, Thomson Scientific, London, GB; AN 2006-030289. XP002622985, & CN 1657023A (Shanghai No. 1 Peoples Hospital), Aug. 24, 2005 *abstract*.
Database WPI, Week 200360, Thomson Scientific, London, GB; AN 2003-628020. XP002622988, & CN 1413594A (Yang W) Apr. 30, 2003 *abstract*.
Office Action, mailed Jun. 5, 2009, for CN Patent Application 200710171085X, 12 pages.

* cited by examiner

*Primary Examiner* — Carlos Azpuru
*Assistant Examiner* — Casey Hagopian
(74) *Attorney, Agent, or Firm* — Schwabe, Williamson & Wyatt, P.C.

(57) ABSTRACT

An arsenic trioxide medical elution scaffold and preparation method thereof, wherein the arsenic trioxide medical elution scaffold comprises scaffold, polymer coating covering the scaffold and arsenic trioxide loaded in the polymer coating which is in the form of single particle or particle conglomeration island. Animal experiments testify that the medical release of the arsenic trioxide medical elution scaffold is suitably uniform, and can be controlled to meet clinic requirement.

17 Claims, 6 Drawing Sheets

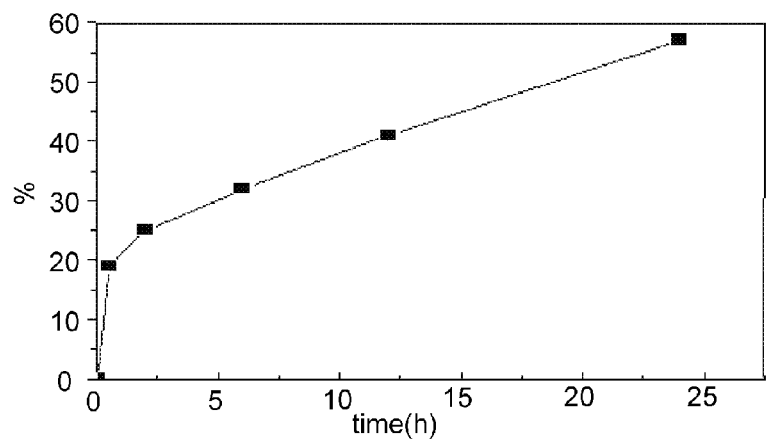
FIG.6
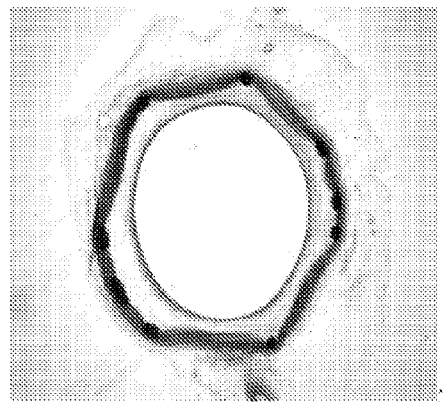 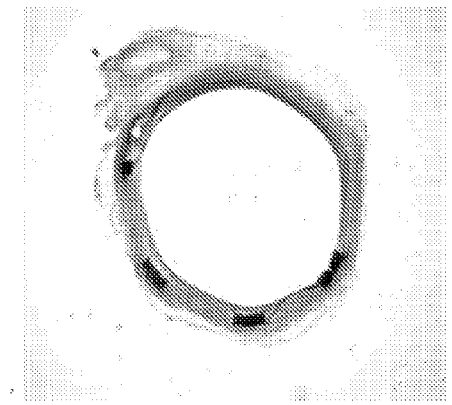
FIG.7  FIG.8
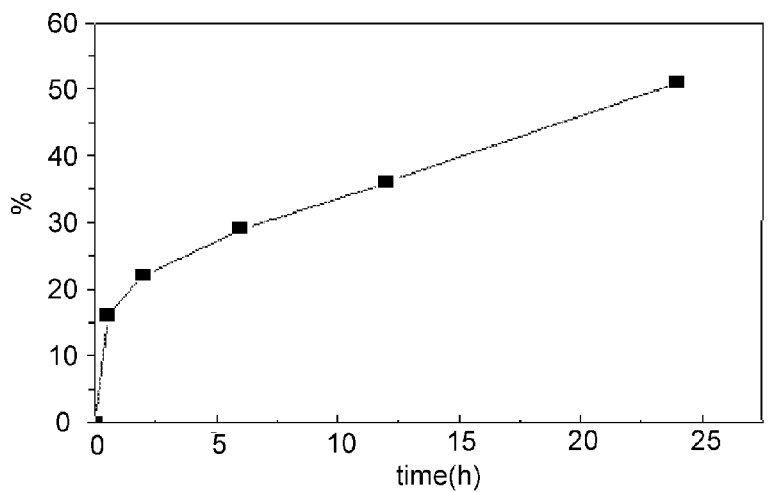
FIG.9

ARSENIC TRIOXIDE MEDICAL ELUTION SCAFFOLD

TECHNICAL FIELD

The present invention relates to a medical scaffold, more particularly, relates to a medical elution scaffold for preventing restenosis after implantation of coronary artery scaffold.

BACKGROUND

Arsenic trioxide ($As_2O_3$) is a main component in the traditional Chinese medicine White Arsenic, and had been used to treat many diseases such as malignant tumor in Chinese medical science.

Natural arsenic compounds have been used as a medicine for more than 2400 years. In 1970s, hematologists used $As_2O_3$ to treat promyelocytic leukemia and notable therapeutic effect was obtained. $As_2O_3$ has also been used to treat solid tumor in recent years. Zhuoqi ZHANG et. al. and Jianwei SHAO et. al. found that $As_2O_3$ had effects of anti-proliferation, apoptosis promotion and cell cycle arrest on VSMCs, and was significant for possibly decreasing cell amount in the new tunica intima at the sites where blood vessel scaffold was implanted in vivo and reducing the thickness of the tunica intima.

On the premise of ensuring medical effect, to reduce the dosage of arsenic trioxide, a highly toxic medicine, as much as possible and to ensure the stability of the medicine amount carried on the scaffold so as to achieve suitable uniformity and controllability for arsenic trioxide release is critical in determining the use value of the arsenic trioxide elution scaffold.

Because of the difference in solubility between the water-soluble medicine arsenic trioxide and the polymer carrier, a characteristic two-phase separation is present during the spraying of the medicine and the carrier. For example, both of the arsenic trioxide spraying techniques disclosed in CN200510023714.5 and CN1413594A employ a process of spraying the medicine and the carrier together after mixing in a solvent. In these techniques, the control of the medicine amount on the scaffold and the uniformity of medicine distribution are restricted due to the settlement of arsenic trioxide (reduction in particle size of arsenic trioxide particles may induce conglomeration of the particles), and irregular channels may form among medicine particles, whereby it is difficult to control the stability of medicine release (see FIG. 1). This leads to a high-dosage of the medicine, poor efficacy on restenosis inhibition, and increased risk in clinical treatment. Several hours after damaging the blood vessel, scaffold and balloon dilatation may stimulate hyperplasia of SMC, which is beneficial for the formation of new tunica intima; several days to several months after the damage, relative deficiency of cell apoptosis during this period is an important reason for formation of restenosis. Therefore, it is necessary to provide desirable and stable medicine release on the scaffold.

SUMMARY OF THE INVENTION

The object of the present invention is to provide an arsenic trioxide medical elution scaffold to overcome the above-mentioned disadvantages in the prior art.

The arsenic trioxide medical elution scaffold according to the present invention comprises scaffold, polymer coating covering the scaffold and arsenic trioxide loaded in the polymer coating, characterized in that arsenic trioxide is loaded in the polymer coating in a form of single particle or isolated and scattered conglomerated particle, i.e., the medicine particles are separated from each other as an "isolated island" structure for the purpose of stable sustained-release of the medicine.

Preferably, the arsenic trioxide particles are embedded in the polymer microspheres.

The single particle, the conglomerated particle or the polymer microsphere with embedded arsenic trioxide particles have a particle size of 0.01 to 50 µm.

The weight ratio of arsenic trioxide to the polymer coating is 0.1:9.9 to 9.9:0.1.

Preferably, the weight ratio of arsenic trioxide to the polymer is 0.2 to 150.0, more preferably 0.5 to 1.5.

Preferably, the content of arsenic trioxide on the scaffold is 0.01 to 3.2 µg/mm$^2$, more preferably 0.47 to 1.11 µg/mm$^2$.

Base material of the scaffold includes stainless steel, cobalt-nickel alloy and other metal or alloy with good biocompatibility.

The polymer is selected from degradable polymers.

The degradable polymer is one or more selected from a group consisting of cellulose, polysaccharide, chitin, chitosan or derivatives thereof, polyhydroxyalkyl alcohol ester, poly(β-malate), poly-α-hydroxyacid esters, polycaprolactone, polycyanoacrylate, or polyamino acid, pseudo-polyamino acid, poly(lactide-co-glycolide) (PLGA), poly (lactic acid), polycarbonate, polyanhydride, polyvinylpyrrolidinone or polyvinylpyrrolidinone, or copolymer thereof.

The scaffold according to the present invention is a routine blood vessel scaffold for implanting, such as balloon dilatation coronary artery scaffold, brain blood vessel scaffold and so on. These scaffolds have been described in details in various documents such as CN1360951, CN1355005 and CN1669595.

One of the methods for preparing the arsenic trioxide medical elution scaffold according to the present invention comprises the following steps:

(1) dissolving the polymer in an organic solvent, dissolving arsenic trioxide in water, and adding a surfactant thereto respectively; mixing these two solution and emulsifying to obtain an emulsion, then spraying the emulsion on the scaffold to obtain a medical coating after evaporation of the solvent; the obtained arsenic trioxide particles have a particle size of 0.01 to 50 µm;

the weight ratio of arsenic trioxide to the polymer in the emulsion is 0.1:9.9 to 9.9:0.1;

the solvent is selected from organic solvents such as tetrahydrofuran, dichloromethane, chloroform, dimethylformamide or DMSO, and the content of the polymer is 1-90% by weight;

the content by weight of arsenic trioxide in the arsenic trioxide aqueous solution is 0.01% to saturation;

the surfactant is one or more selected from a group consisting of the SPAN series (nonionic emulsifying, dispersing, solubilizing and wetting agents sold under the trademark SPAN) and the TWEEN series (nonionic emulsifying, dispersing, solubilizing and wetting agents sold under the trademark TWEEN), SPAN 60 or SPAN 80 is preferred in the SPAN series and TWEEN 60 or TWEEN 80 is preferred in the TWEEN series, and the amount added is 0.01-1% by weight of the degradable polymer;

(2) leveling the polymer on the surface of the emulsion particles with a liquid solvent or a gas solvent, or spraying a new coating on the scaffold, and then drying in vacuum, at this time arsenic trioxide is fixed in the polymer coating in a form of "isolated island" structure, so as to obtain the arsenic trioxide medical elution scaffold.

Another method for preparing the arsenic trioxide medical elution scaffold according to the present invention comprises the steps of:

dissolving the polymer in an organic solvent, suspending the arsenic trioxide particles having a particle size of 0.01 to 50 μm in alcohol, adding a surfactant thereto; adding the mixture into the polymer solution and stirring to form a polymer thin film on the surface of $As_2O_3$ and form an emulsion; spraying the emulsion on the surface of the scaffold and drying to obtain the arsenic trioxide elution scaffold in which arsenic trioxide is fixed in the polymer coating in a form of "isolated island" structure.

The content of arsenic trioxide in alcohol is 0.01 to 50 g/ml, and the concentration by weight of the polymer in the organic solvent is 0.01-50%;

the weight ratio of arsenic trioxide to the polymer in the emulsion is 0.1:9.9 to 9.9:0.1;

the surfactant is selected from a composition of the SPAN series (such as SPAN 60 and SPAN 80) and the TWEEN series (such as TWEEN 60 and Tween 80), and the amount added can be 0.01-1% by weight of the degradable polymer.

Still another method for preparing the arsenic trioxide medical elution scaffold according to the present invention comprises the following steps:

spraying the arsenic trioxide aqueous solution and the organic solvent containing the polymer on the scaffold respectively for several times, namely in a sandwich form, with one layer of the polymer solution on one layer of the arsenic trioxide aqueous solution coating, and so forth; and leveling the polymer with a liquid solvent or a gas solvent each time after coating the polymer solution to enwrap a layer of the polymer on the surface of the arsenic trioxide particles, at this time arsenic trioxide is fixed in the polymer coating in a form of "isolated island" structure, then drying to obtain the arsenic trioxide medical elution scaffold.

The solvent is selected from organic solvents such as tetrahydrofuran, dichloromethane, chloroform, dimethylformamide or DMSO, and the content of the polymer in the organic solvent is 1-90% by weight;

the concentration by weight of the arsenic trioxide aqueous solution is 0.01% to saturation;

spraying amount of the arsenic trioxide aqueous solution and that of the organic solvent containing the polymer are controlled so that the weight ratio of arsenic trioxide to the polymer in the coating is 0.1:9.9 to 9.9:0.1.

Yet still another method for preparing the arsenic trioxide medical elution scaffold according to the present invention comprises the following steps:

(1) drilling micropores on the surface of the scaffold by a laser method; mixing the arsenic trioxide particles and an organic solvent containing the polymer to suspend the arsenic trioxide particles in the organic solvent containing the polymer, then coating the polymer solution with medicine in the micropores in the scaffold using sited feeding method; the surface can be coated or not coated with sustained-release controlled coating.

The solvent is selected from organic solvents such as tetrahydrofuran, dichloromethane, chloroform, dimethylformamide or DMSO, in the organic solvent, the concentration by weight of the polymer in the solvent is 0.01% to 90%, and the weight ratio of arsenic trioxide to the polymer is 0.1:9.9 to 9.9:0.1.

The release properties of the medicine in the present invention can be measured by the method disclosed in "Preparation and the release characteristic in vitro of arsenic trioxide albumin nanospheres", Jie ZHOU, Puqing ZENG, Xiang GAO, Shusheng XIE, and Shuli WEI, Chinese Journal of New Drugs, 2005, 14(1), 54-57.

The animal experiments prove that the medicine release of the arsenic trioxide medical elution scaffold according to the present invention is suitably uniform and controllable to meet the requirements of clinical application.

BRIEF DESCRIPTION OF THE DRAWINGS

FIG. 6 shows the release result of the medicine on the scaffold in Example 2.
FIG. 7 shows the blood vessel section in the animal experiment of the scaffold in Example 2.
FIG. 8 shows the blood vessel section in the animal experiment of the scaffold in Example 2.
FIG. 9 shows the release result of the medicine on the scaffold in Example 3.

DETAILED DESCRIPTION OF THE INVENTION

Example 1

Figure 1:
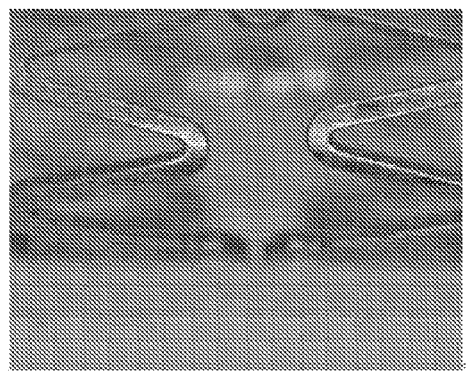
FIG. 1 shows the scaffold prepared in the prior art.
Figure 2:
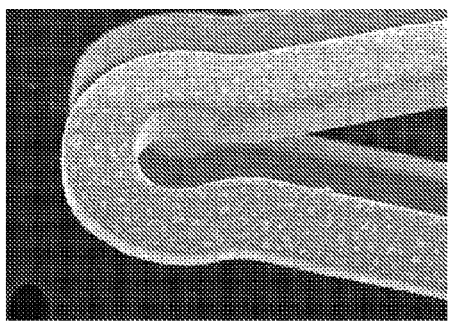
FIG. 2 shows photograph of the scaffold in Example 1.

$As_2O_3$ (0.30 g) was milled into particles having an average particle size of 0.10 μm which were suspended in anhydrous alcohol (100 ml), and surfactant SPAN 80 (0.005 g) was added thereto. Polycaprolactone (2.5 g) was dissolved in tetrahydrofuran solution (100 ml), then the alcohol solution containing the arsenic trioxide particles was added to the polycaprolactone solution and dispersed therein under stirring, and then anhydrous alcohol (80 ml) was added dropwise thereto under stirring to form a thin film of polycaprolactone on the surface of the $As_2O_3$ particles, and a suspension was formed when the particles precipitated in a form of microcapsules. Upon being sprayed uniformly with the suspension on the surface, the 316 stainless steel scaffold was dried in vacuum at 80° C. for 8 h to give the $As_2O_3$ elution scaffold, wherein the content of $As_2O_3$ was 0.05 µg/mm² and $As_2O_3$ was fixed on the polymer coating in a form of "isolated island" structure, as indicated in FIG. 2.

Figure 3:
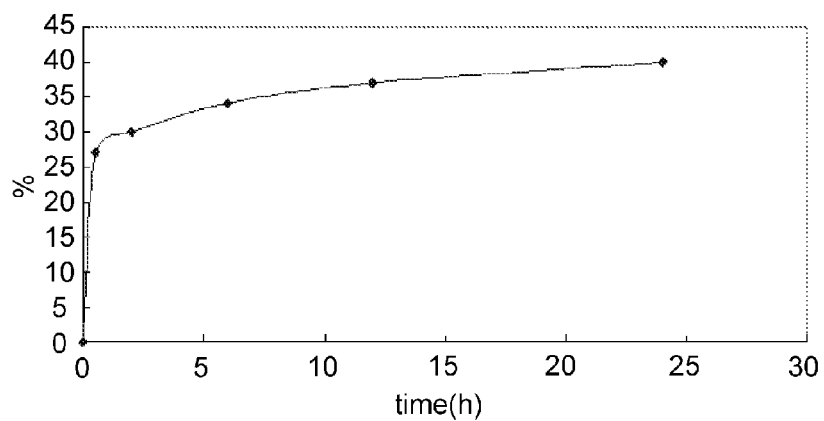
FIG. 3 shows the release result of the medicine on the scaffold in Example 1.

Antibody cd133 was coated on the surface of the scaffold to adsorb endothelial progenitor cells in order to accelerate the repair of the endothelium. The release results were shown in FIG. 3.

The above-mentioned $As_2O_3$ medical elution scaffold was subjected to animal experiments, and the experimental method was as follows:

three-month-old mini-pigs were used as the experimental samples. 20 mg/kg ketamine was injected intravenously to achieve general anesthesia, after disinfection and draping on the right-side groin, the femoral artery was separated and cut open, a 7F arterial sheath was placed therein, and 7F-guided ductal type coronary angiography was conducted; a 0.014" BMW guidewire was guided to the distal end of the coronary artery (RCA, LAD, LCX), and the scaffold was delivered along the guidewire, and then released with the expansion of balloon at certain pressure. After the balloon, the guidewire, the duct and the arterial sheath were removed, the groin was sutured.

The animals were sacrificed after three months and hearts were harvested; the scaffold was embedded in resin and then prepared as hard issue sections. After stained with hematoxylin and eosin respectively, the sections were photographed under a microscope and the area and thickness of the tunica intima were calculated.

Figure 4:
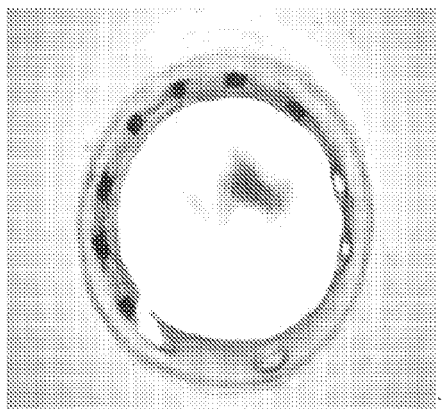
FIG. 4 shows the blood vessel section in the animal experiment of the scaffold in Example 1.
Figure 5:
FIG. 5 shows the blood vessel section in the animal experiment of the scaffold in Example 1.

The results of the 3-month animal experiment show that the thickness of the blood vessel tunica intima was 152±41 µm, and the blood vessel sections were shown in FIG. 4 and FIG. 5. No thrombus or hemangioma was observed.

Example 2

$As_2O_3$ (1.0 g) was milled into particles having an average particle size of 15 µm which were suspended in anhydrous alcohol (100 ml), and surfactant SPAN 80 (0.005 g) was added thereto. Poly(lactide-co-glycolide) (0.2 g, with the weight ratio of glycolide:lactide=2:8) was dissolved in chloroform solution (100 ml), then the alcohol solution containing the arsenic trioxide particles was added to the PLGA solution and dispersed therein under stirring, and then anhydrous alcohol (200 ml) was added dropwise thereto under stirring to form a thin film of PLGA on the surface of the $As_2O_3$ particles, and a suspension was formed when the particles precipitated in a form of microcapsules. Upon being sprayed uniformly with the suspension on the surface, the nickel-cobalt alloy scaffold was dried in vacuum at 80° C. for 8 h to give the $As_2O_3$ elution scaffold, wherein the content of $As_2O_3$ was 2.65 µg/mm² and $As_2O_3$ was fixed in the polymer coating in a form of "isolated island" structure.

A polylactic acid sustained-release layer containing heparin was coated on the surface of the scaffold to prevent formation of acute thrombus and to control sustained-release of the medicine efficiently. The release results were shown in FIG. 6.

The above-mentioned $As_2O_3$ medical elution scaffold was subjected to animal experiments. The experimental results show that the thickness of the blood vessel tunica intima was 161±38 µm, and the blood vessel sections were shown in FIG. 7 and FIG. 8. No thrombus or hemangioma was observed.

Example 3

$As_2O_3$ (1.0 g) was milled into particles having an average particle size of 0.25 µm which were suspended in anhydrous alcohol (100 ml), then surfactant TWEEN 80 (0.0025 g) was added thereto. Polylactic acid (1.0 g) was dissolved in a dichloromethane solution (100 ml), then the alcohol solution containing the arsenic trioxide particles was added to the polylactic acid solution and dispersed therein under stirring, and then anhydrous alcohol (125 ml) was added dropwise thereto under stirring to form a thin film of polylactic acid on the surface of the $As_2O_3$ particles, and a suspension was formed when the particles precipitated in a form of microcapsules. Upon being sprayed uniformly with the suspension on the surface, the 316 stainless steel scaffold was dried in vacuum at 80° C. for 8 h to give the $As_2O_3$ elution scaffold, wherein the content of $As_2O_3$ was 0.52 µg/mm², the weight ratio of the medicine to the polymer was 1:1, and $As_2O_3$ was fixed in the polymer coating in a form of "isolated island" structure. The release results were shown in FIG. 9.

Figure 10:
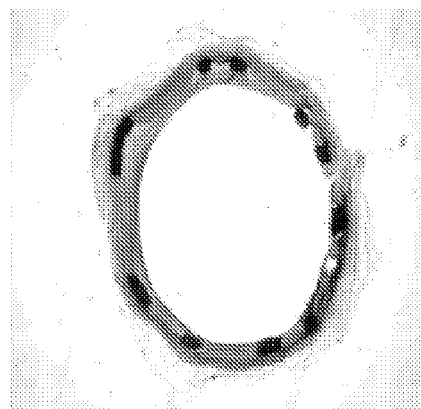
FIG. 10 shows the blood vessel section in the animal experiment of the scaffold in Example 3.
Figure 11:
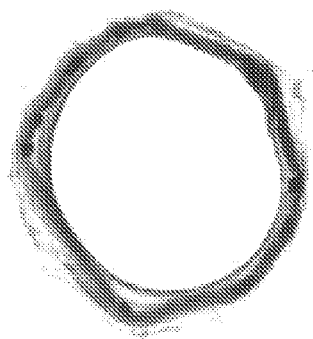
FIG. 11 shows the blood vessel section in the animal experiment of the scaffold in Example 3.

The above-mentioned $As_2O_3$ medical elution scaffold was subjected to animal experiments. The experimental results show that the thickness of the blood vessel tunica intima was 128±25 µm, and the blood vessel sections were shown in FIG. 10 and FIG. 11. No thrombus or hemangioma was observed.

Example 4

Figure 12:
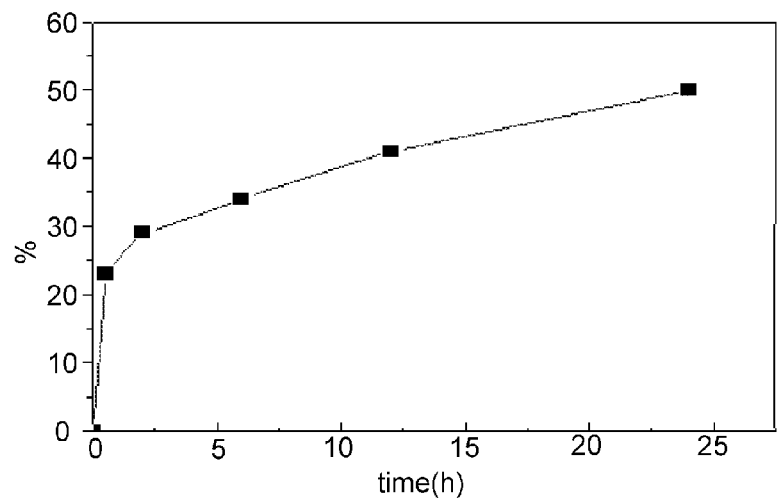
FIG. 12 shows the release result of the medicine on the scaffold in Example 4.

Poly(lactide-co-glycolide) (1 g, weight ratio of glycolide:lactide=1:1) copolymer was dissolved in a chloroform solution (100 ml), and surfactant SPAN 80 (0.098 g) was added and mixed therewith to form an oil phase; surfactant TWEEN 80 (0.002 g) was added to a saturated aqueous solution of $As_2O_3$ (50 ml) to form an aqueous phase. The aqueous phase was added to the oil phase and dispersed uniformly under stirring at 3000 rpm to form an emulsion. Upon being sprayed with the emulsion on the surface, the scaffold was dried in vacuum at 75° C. for 10 h to form the $As_2O_3$ elution scaffold, wherein the content of $As_2O_3$ was 50 µg and $As_2O_3$ was fixed in the polymer coating in a form of "isolated island" structure. Antibody cd133 was coated on the surface of the scaffold to adsorb endothelial progenitor cells in order to accelerate the repair of the endothelium. The release results were shown in FIG. 12.

Figure 13:
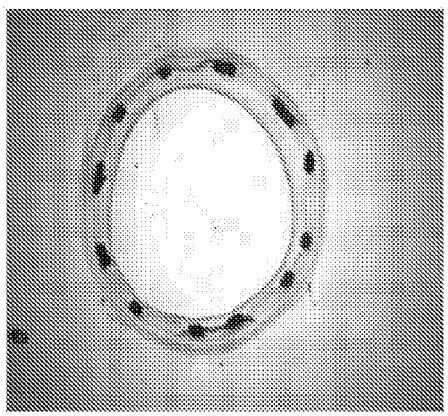
FIG. 13 shows the blood vessel section in the animal experiment of the scaffold in Example 4.
Figure 14:
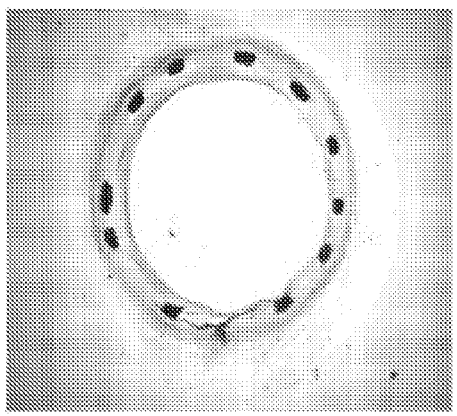
FIG. 14 shows the blood vessel section in the animal experiment of the scaffold in Example 4.

The results of the 3-month animal experiment show that the thickness of the blood vessel tunica intima was 143±49 µm, and the blood vessel sections were shown in FIG. 13 and FIG. 14. No thrombus or hemangioma was observed.

Example 5

Figure 15:
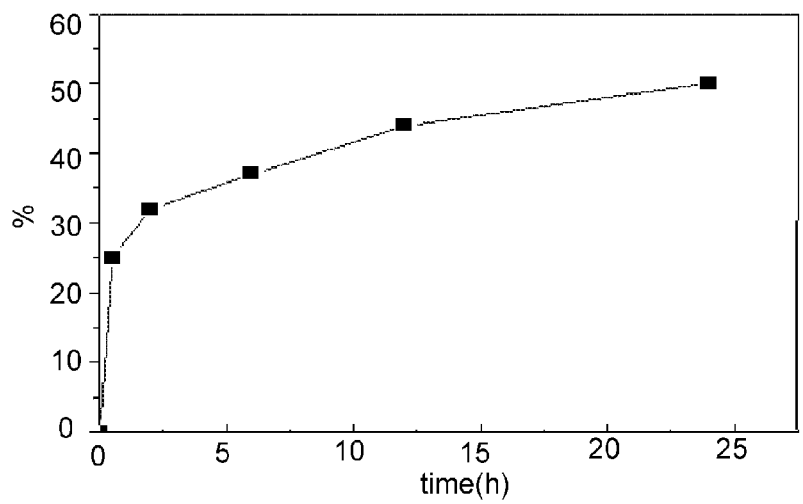
FIG. 15 shows the release result of the medicine on the scaffold in Example 5.

Polylactic acid (0.1 g) was dissolved in a chloroform solution (100 ml), and surfactant SPAN 80 (0.098 g) was added and mixed therewith to form an oil phase; surfactant Tween 80 (0.002 g) was added to a saturated aqueous solution of $As_2O_3$ (50 ml) to form an aqueous phase. The aqueous phase was added to the oil phase and dispersed uniformly under stirring at 3000 rpm to form an emulsion. Upon being sprayed with the emulsion on the surface, the scaffold was dried in vacuum at 75° C. for 10 h to form the $As_2O_3$ elution scaffold, wherein the content of $As_2O_3$ was 0.81 µg/mm² and $As_2O_3$ was fixed in the polymer coating in a form of "isolated island" structure. Antibody cd134 was coated on the surface of the scaffold to adsorb endothelial progenitor cells in order to accelerate the repair of the endothelium. The release results were shown in FIG. 15.

Figure 16:
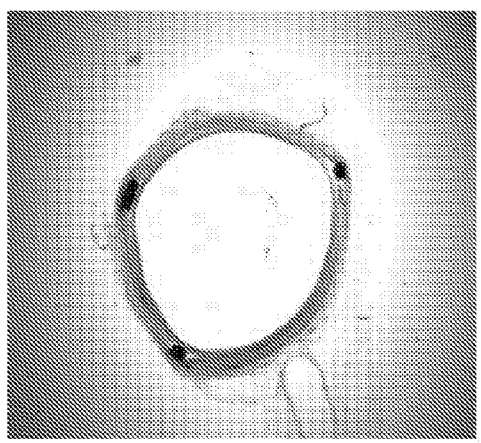
FIG. 16 shows the blood vessel section in the animal experiment of the scaffold in Example 5.
Figure 17:
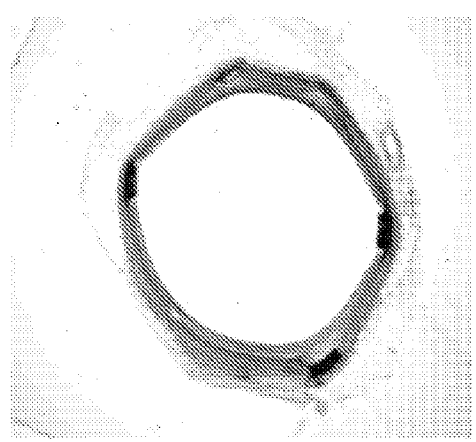
FIG. 17 shows the blood vessel section in the animal experiment of the scaffold in Example 5.

The results of the 3-month animal experiment show that the thickness of the blood vessel tunica intima was 143±49 μm, and the blood vessel sections were shown in FIG. 16 and FIG. 17. No thrombus or hemangioma was observed.

Example 6

Figure 18:
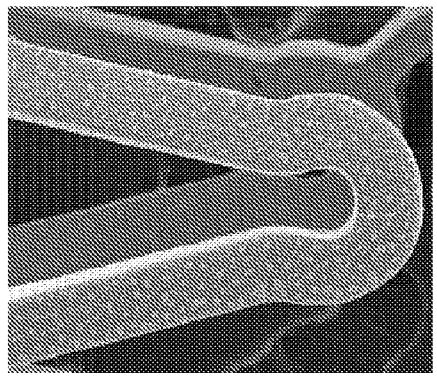
FIG. 18 shows photograph of the scaffold in Example 6.

Polycaprolactone (0.1 g) was dissolved in chloroform (100 ml), and $As_2O_3$ (1.0 g) was dissolved in redistilled water (100 ml). Firstly the polymer solution was sprayed on the surface of the scaffold, and then the $As_2O_3$ aqueous solution was sprayed thereon. Upon drying, $As_2O_3$ formed conglomerated particles on the surface of the scaffold, and a solvent was sprayed on the surface of the scaffold to level the polymer coating. Enwrapping of the polymer was formed on the surface of the $As_2O_3$ microparticles, and $As_2O_3$ was fixed in the polymer coating in a form of "isolated island" structure, as indicated in FIG. 18.

Figure 19:
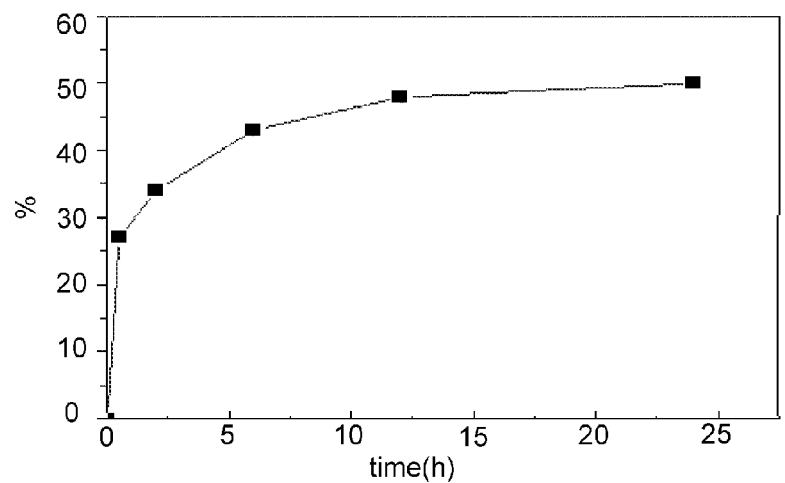
FIG. 19 shows the release result of the medicine on the scaffold in Example 6.

After drying, the polymer solution, the $As_2O_3$ aqueous solution and the solvent were sprayed in this order until the medicine content achieved a desired amount. The content of $As_2O_3$ was 1.25 μg/mm². The release results were shown in FIG. 19.

Figure 20:
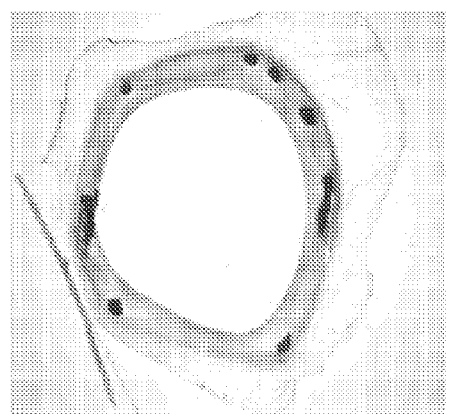
FIG. 20 shows the blood vessel section in the animal experiment of the scaffold in Example 6.
Figure 21:
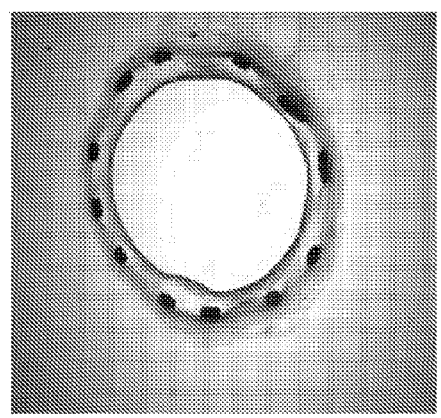
FIG. 21 shows the blood vessel section in the animal experiment of the scaffold in Example 6.

The results of the 3-month animal experiment show that the thickness of the blood vessel tunica intima was 141±44 μm, and the blood vessel sections were shown in FIG. 20 and FIG. 21, no thrombus or hemangioma was observed. After 12 weeks of the scaffold implantation, no obvious hyperplasia can be observed in the blood vessel tunica intima, the area of cavity was increased distinctly, while not a single thrombus or hemangioma occurred; the surface of the scaffold was fully covered by endothelium; the tunica intima, tunica media and tunica adventitia of the blood vessel were clear, and no obvious inflammation was observed. The results were shown in FIG. 20 and FIG. 21.

Example 7

Figure 22:
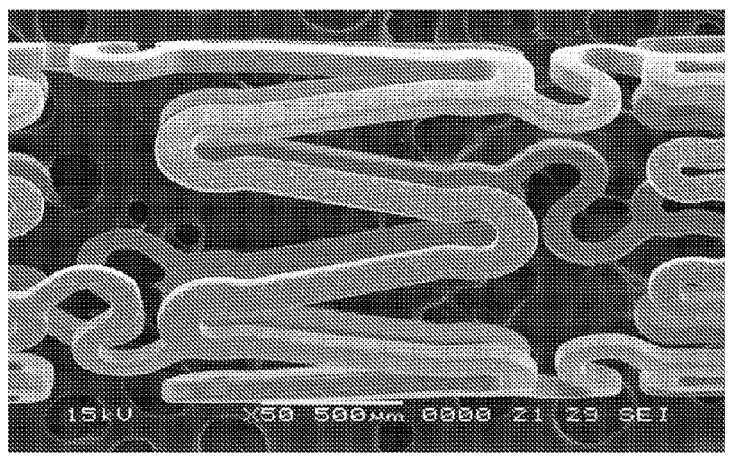
FIG. 22 shows photograph of the scaffold in Example 7.
Figure 23:
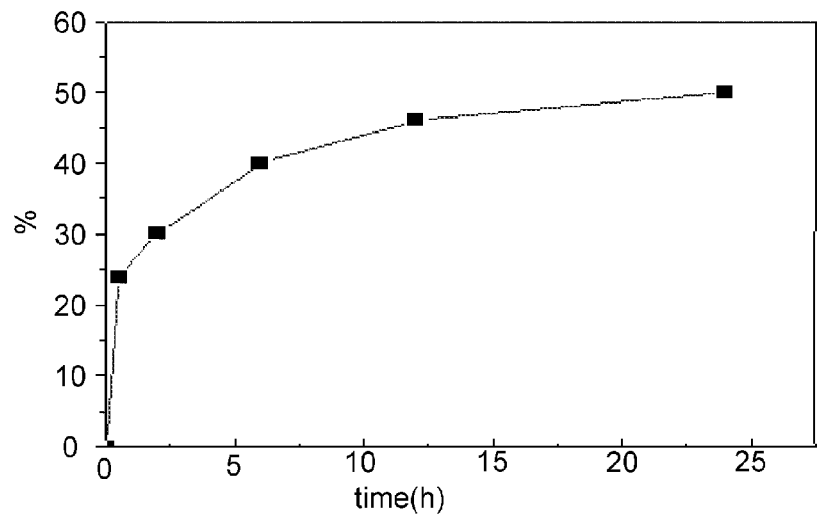
FIG. 23 shows the release result of the medicine on the scaffold in Example 7.

10 μm micropores were etched on the outer surface of the scaffold (the surface of the scaffold in contact with blood vessels after being implanted in vivo) with a laser etching machine. An emulsion was prepared with the method for preparing emulsion as described in Example 1, and the emulsion was distilled under reduced pressure to achieve a concentration of the microparticles of 30% by weight. The solution was injected into the micropores, and after evaporation of the solvent, $As_2O_3$ was fixed in the polymer coating in a form of "isolated island" structure on the outer surface of the scaffold, as indicated in FIG. 22. After drying in vacuum, the $As_2O_3$ medical elution scaffold was obtained. The content of $As_2O_3$ was 2.4 μg/mm². The release results were shown in FIG. 23.

Figure 24:
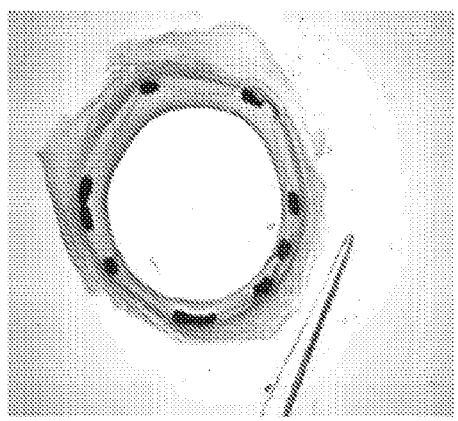
FIG. 24 shows the blood vessel section in the animal experiment of the scaffold in Example 7.
Figure 25:
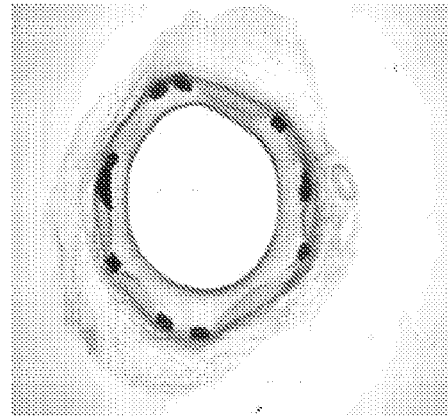
FIG. 25 shows the blood vessel section in the animal experiment of the scaffold in Example 7.

The results of the 3-month animal experiment show that the thickness of the blood vessel tunica intima was 128±35 μm, and the blood vessel sections were shown in FIG. 24 and FIG. 25 with no thrombus or hemangioma observed inside the scaffold. The surface of the scaffold was fully covered by endothelium; the tunica intima, tunica media and tunica adventitia of the blood vessel were clear, and no obvious inflammation was observed.

The invention claimed is:

1. An arsenic trioxide medical elution scaffold comprising a scaffold, a polymer coating covering the scaffold and arsenic trioxide loaded in the polymer coating, characterized in that the arsenic trioxide is loaded in the polymer coating as single particles or as isolated and scattered conglomerated particles, wherein at least a portion of the single particles or conglomerated particles are embedded in polymer microspheres, the single particles, the conglomerated particles or the polymer microspheres with embedded arsenic trioxide particles having a particle size of 0.01 to 50 μm, the weight ratio of arsenic trioxide to the polymer being 0.5 to 1.5, the content of arsenic trioxide being 0.47-1.11 μg/mm², and the polymer being a degradable polymer,
wherein the degradable polymer is one or more polymers selected from the group consisting of polysaccharide, polyhydroxyalkyl alcohol ester, poly(β-malate), poly-α-hydroxyacid esters, polyamino acid, pseudo-polyamino acid, polycarbonate, and polyanhydride.

2. The arsenic trioxide medical elution scaffold according to claim 1, characterized in that a base material of the scaffold includes at least one of stainless steel or a cobalt-nickel alloy.

3. The arsenic trioxide medical elution scaffold according to claim 1, characterized in that the scaffold is a blood vessel scaffold for implanting.

4. The arsenic trioxide medical elution scaffold according to claim 1, wherein the poly-α-hydroxyacid ester is one or more polymers selected from the group consisting of polycaprolactone, poly(lactide-co-glycolide) (PLGA), and poly (lactic acid).

5. A method for preparing an arsenic trioxide medical elution scaffold, the method comprising:
(1) dissolving a polymer in an organic solvent and dissolving arsenic trioxide in water, then adding a surfactant thereto respectively, wherein the polymer is a degradable polymer, the degradable polymer being one or more polymers selected from the group consisting of polysaccharide, polyhydroxyalkyl alcohol ester, poly(β-malate), poly-α-hydroxyacid esters, polyamino acid, pseudo-polyamino acid, polycarbonate, and polyanhydride;
mixing these two solutions and emulsifying to obtain an emulsion having a weight ratio of arsenic trioxide to degradable polymer of 0.5 to 1.5, then spraying the emulsion onto a scaffold to obtain a medical coating after evaporation of the solvent, the medical coating comprising single arsenic trioxide particles or isolated and scattered conglomerated arsenic trioxide particles, at least a portion of the arsenic trioxide particles being embedded within polymer microspheres, and the single or conglomerated arsenic trioxide particles or the polymer microspheres with embedded arsenic trioxide particles having a particle size of 0.01 to 50 μm;
(2) leveling the polymer on the surface of the emulsion particles with a liquid solvent or a gas solvent, or spraying a new coating on the scaffold, then drying to obtain the arsenic trioxide medical elution scaffold, wherein the weight ratio of arsenic trioxide to the polymer is 0.5 to 1.5 and the content of arsenic trioxide on the scaffold is 0.47-1.11 μg/mm².

6. The method according to claim 5, wherein the solvent is selected from a group consisting of tetrahydrofuran, dichloromethane, chloroform, dimethylformamide or DMSO.

7. The method according to claim 5, wherein the poly-α-hydroxyacid ester is one or more polymers selected from the group consisting of polycaprolactone, poly(lactide-co-glycolide) (PLGA), and poly(lactic acid).

8. A method for preparing an arsenic trioxide medical elution scaffold, the method comprising:
dissolving a polymer in an organic solvent, wherein the polymer is a degradable polymer, the degradable polymer being one or more polymers selected from the group consisting of polysaccharide, polyhydroxyalkyl alcohol ester, poly(β-malate), poly-α-hydroxyacid esters, polyamino acid, pseudo-polyamino acid, polycarbonate, and polyanhydride;

suspending arsenic trioxide particles in alcohol, adding a surfactant thereto, adding the suspension to the polymer solution and stirring to form a polymer thin film on the surface of $As_2O_3$ to form an emulsion, and then spraying the emulsion on the surface of the scaffold and drying to form a medical coating having single arsenic trioxide particles or isolated and scattered conglomerated arsenic trioxide particles and thereby obtain the arsenic trioxide elution scaffold, at least a portion of the arsenic trioxide particles being embedded within polymer microspheres, and the single or conglomerated arsenic trioxide particles or the polymer microspheres with embedded arsenic trioxide particles having a particle size of 0.01 to 50 μm, wherein the weight ratio of arsenic trioxide to the polymer is 0.5 to 1.5, and wherein the content of arsenic trioxide on the scaffold is 0.47-1.11 $\mu g/mm^2$.

9. The method according to claim 8, characterized in that in alcohol, the content of arsenic trioxide is 0.01 to 50 g/ml; in the organic solvent, the polymer has a concentration by weight of 0.01% to 50%;

and the amount of the surfactant added is 0.01% by weight to 1% by weight of the degradable polymer.

10. The method according to claim 8, wherein the poly-α-hydroxyacid ester is one or more polymers selected from the group consisting of polycaprolactone, poly(lactide-co-glycolide) (PLGA), and poly(lactic acid).

11. A method for preparing an arsenic trioxide medical elution scaffold, the method comprising:

spraying an arsenic trioxide aqueous solution and an organic solvent containing a polymer onto a scaffold respectively several times with one layer of the polymer solution on one layer of the arsenic trioxide aqueous solution coating, wherein the arsenic trioxide is loaded in the layer of the arsenic trioxide aqueous solution coating as single arsenic trioxide particles or isolated and scattered conglomerated arsenic trioxide particles, the single or conglomerated arsenic trioxide particles having a particle size of 0.01 to 50 μm, wherein the polymer is a degradable polymer, and the degradable polymer is one or more polymers selected from the group consisting of polysaccharide, polyhydroxyalkyl alcohol ester, poly(β-malate), poly-α-hydroxyacid esters, polyamino acid, pseudo-polyamino acid, polycarbonate, and polyanhydride;

leveling the polymer with a liquid solvent or a gas solvent each time after coating the polymer solution to enwrap a layer of the polymer on the surface of the arsenic trioxide particles; then drying in vacuum to obtain the arsenic trioxide medical elution scaffold, wherein the weight ratio of arsenic trioxide to the polymer is 0.5 to 1.5 and content of arsenic trioxide on the scaffold is 0.47-1.11 $\mu g/mm^2$.

12. The method according to claim 11, characterized in that the solvent is selected from a group consisting of tetrahydrofuran, dichloromethane, chloroform, dimethylformamide or DMSO, and the content of the polymer in the organic solvent is 1 to 90% by weight; and the concentration by weight of the arsenic trioxide aqueous solution is 0.01% to saturation.

13. The method according to claim 11, wherein the poly-α-hydroxyacid ester is one or more polymers selected from the group consisting of polycaprolactone, poly(lactide-co-glycolide) (PLGA), and poly(lactic acid).

14. A method for preparing an arsenic trioxide medical elution scaffold, the method comprising:

(1) drilling micropores on the surface of a scaffold by a laser method, mixing arsenic trioxide particles and an organic solvent containing a polymer to suspend the arsenic trioxide particles in the organic solvent containing the polymer, then coating the polymer solution comprising medicine into the micropores in the scaffold, wherein the arsenic trioxide particles are single arsenic trioxide particles or isolated and scattered conglomerated arsenic trioxide particles, at least a portion of the arsenic trioxide particles being embedded in polymer microspheres, the single or conglomerated arsenic trioxide particles or the polymer microspheres with embedded arsenic trioxide particles having a particle size of 0.01 to 50 μm, the weight ratio of arsenic trioxide to the polymer being 0.5 to 1.5, the content of arsenic trioxide in the scaffold being 0.47-1.11 $\mu g/mm^2$, and the polymer being a degradable polymer, wherein the degradable polymer is one or more polymers selected from the group consisting of polysaccharide, polyhydroxyalkyl alcohol ester, poly(β-malate), poly-α-hydroxyacid esters, polyamino acid, pseudo-polyamino acid, polycarbonate, and polyanhydride.

15. The method according to claim 14, characterized in that the organic solvent is selected from a group consisting of tetrahydrofuran, dichloromethane, chloroform, dimethylformamide or DMSO, and in the organic solvent, the concentration by weight of the polymer in the solvent is 0.01 to 90%.

16. The method of claim 14, further comprising adding a sustained-release coating to the surface of the scaffold.

17. The method according to claim 14, wherein the poly-α-hydroxyacid ester is one or more polymers selected from the group consisting of polycaprolactone, poly(lactide-co-glycolide) (PLGA), and poly(lactic acid).

* * * * *